United States Patent [19]

Fortunato et al.

[11] Patent Number: 4,732,480
[45] Date of Patent: Mar. 22, 1988

[54] INTERFEROMETRIC DEVICE FOR DETECTING GAS

[75] Inventors: Gerard Fortunato; Dominique Laurent, both of Lyons, France

[73] Assignee: Elf France, Courbevoie, France

[21] Appl. No.: 853,038

[22] Filed: Apr. 17, 1986

[30] Foreign Application Priority Data

Apr. 25, 1985 [FR] France ............................... 85 06349

[51] Int. Cl.$^4$ .......................... G01B 9/02; G01J 3/45
[52] U.S. Cl. ..................................... 356/346; 356/351
[58] Field of Search ............... 356/351, 365, 367, 334, 356/346; 250/373

[56] References Cited

U.S. PATENT DOCUMENTS

| | | | |
|---|---|---|---|
| 2,823,577 | 2/1958 | Machler | 356/307 |
| 3,216,313 | 11/1965 | Chisholm | 356/334 |
| 3,849,001 | 11/1974 | Inoue et al. | |
| 4,285,596 | 8/1981 | Landa | 356/308 |
| 4,320,973 | 3/1982 | Fortunato et al. | 356/346 |
| 4,480,916 | 11/1984 | Bareket et al. | 356/351 |

FOREIGN PATENT DOCUMENTS 2300998 2/1973 France .
957737 5/1964 United Kingdom .

OTHER PUBLICATIONS

LaGrande Encyclopédie, "Interférences" by Gerard Fortunato, Librairie Larousse 1974, vol. 11, pp. 6387 and 6389.
Born and Wolf, Principle of Optics, 1980, p. 143.
Journal of the Optical Society of America, "Piezo-Optical Birefrigence Modulators: New Use of a Long-Known Effect", vol. 59, No. 8, part 1, Aug. 1969, pp. 950-954.
Journal of Optics, "Application de la Correlation Interferentielle de Spectres a la Detection de Polluants Atmospheriques", vol. 9, No. 5, 1978, pp. 281-290.
Optical Engineering, "The Slective Modulation Interferometric Spectrometer", vol. 17, No. 1, Jan./Feb. 1978, pp. 73-81.

Primary Examiner—Davis L. Willis
Assistant Examiner—Matthew W. Koren
Attorney, Agent, or Firm—Birch, Stewart, Kolasch & Birch

[57] ABSTRACT

Interferometric device for the detection and/or analysis of gas, of the type comprising an optical assembly forming the image of a light source on the sensitive element of the detector, comprising a photoelastic modulator comprising a silica or fluorine plate associated to a piezoelectric ceramic to vibrate in order to give the plate a birefringency variable by compression, having an axis parallel to that of a birefringent plate and an interferential filter constituted by a grating multiplexer device; and having application to the interferometric detection of gas through high-sensitivity.

6 Claims, 4 Drawing Figures

INTERFEROMETRIC DEVICE FOR DETECTING GAS

BACKGROUND OF THE INVENTION

1. Field of the Invention

The present invention concerns an interferometric device for detecting the presence of gas and concerns, in particular, a highly sensitive device allowing the analysis of several gases.

2. Summary of the Prior Art

Interferometric devices for the analysis and/or distribution of gas or the identification of these gases are known.

A birefrigerent plate between two polarizing elements associated with an interferential filter are utilized as interferometric means, these means being provided so as to adjust the thickness of the birefrigerant plate thereby adjusting the path difference introduced by this plate. Effect is made, for example, of the controlled temperature of this plate.

One of the polarizing elements is rotated in order to ensure the modulation of the system at the output of which is disposed a detector supplying a signal during analysis.

Thus, in a prior art device, the image of a light source emitting in the ultraviolet range is formed on the detector, through a cell containing the gas to be analyzed and the interferometric and modulation means described hereinabove.

Such a device, utilizing as polarizing elements the polarizing films, for example, "Polaroid ®", one of which rotates, is perfectly adapted for measuring the emission. However, it is desirable to use a device presenting a greater sensitivity and, furthermore, which can be utilized without requiring any modification for the detection of several gases.

Therefore, in the prior art devices, certain of the components offer relatively poor performances. The polarizers, in particular, to the extent that they are constituted by polarizing films, have a relatively high absorption rate and a poor extinction rate.

Furthermore, the interferential filter utilized in the prior art device has the drawback of presenting, in the ultraviolet range, a very low transmission rate, of 10 to 15%, and also of allowing a considerable amount of stray light to pass. This stray light creates a noise which can drown out the weak signals.

SUMMARY OF THE INVENTION

The aim of the present invention is to supply a device for the detection of gas through an interferometry process presenting high sensitivity.

As will be explained hereinbelow, the device according to the invention allows analysis of several gases to be simply carried out.

An interferometric device according to the invention for the detection of and/or the analysis of gas in a gaseous mixture, of the type comprising an optical assembly forming the image of a light source on the sensitive element of a detector that delivers a response signal, this image being formed through a cell containing the gaseous mixture to be analyzed which is followed by an interferometric unit comprising an interferential filter and a birefringent plate between a polarizer and an analyser, and furthermore comprising modulation means, wherein the polarizer and the analyser together constitute two polarizing prisms, the optical axes of which are normal to that of the device and each giving two photometrically identical, but rectilinearly and perpendicularly polarized images.

For the modulation of the signal, it is not convenient to cause one of the prisms to rotate, so that it is possible to utilize a half-wave plate rotating around the optical axis of the device. It is known, however, that the rotation of an optical component in a light beam always provokes a stray modulation which can become extremely troublesome, especially when it is desired to detect very low signals.

The invention foresees constituting modulation means through the use of a photoelastic modulator comprising a silica or fluorine plate excited by a piezoelectric ceramic in such a way as to give said plate a birefraction variable by compression. It is therefore possible to suppress all stray modulation.

Among the prior art drawbacks inherent in the devices is the very low transmission rate of the interferential filter in the ultraviolet range of 10 to 15%, this filter also presenting band spectrum "feet" which allow a considerable amount of stray light to pass. This light creates a noise that can drown out the weak signals.

The invention foresees replacing the interferential filter of the prior art devices with a holographic or engraved grating, for example, for the ultraviolet range between 180 and 1.000 nm for a concave holographic grating having a small radius of curvature, with an input slot that is the image of a source slot associated to the light source, and an output slot conjugated to the input slot and placed opposite the detector.

The small radius of curvature, which is about 100 m, allows an important transmission of about 400% and cut-out frequencies of this system are perfectly defined, as well as its pass band, thereby fully justifying its utilization as a filter.

Furthermore, cut-out and pass band frequencies can be adjusted by changing the widths of the slots, and with this device, it is possible to block upon several spectral fields, either by maintaining the slots steady and causing the grating to rotate, or by disposing several output slots corresponding to the spectral fields that have been chosen and then by selecting them through successive screenings of the different fields.

As will be seen hereinbelow, it is also possible to utilize a plane grating, in a more general manner and grating dismultiplexer device may be used.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The objects, features and advantages of the present invention will become more apparent from reading the following description given by way of non-limitative illustration, with reference to the appended drawings in which.

DETAILED DESCRIPTION OF THE PREFERRED EMBODIMENTS

Figure 1:
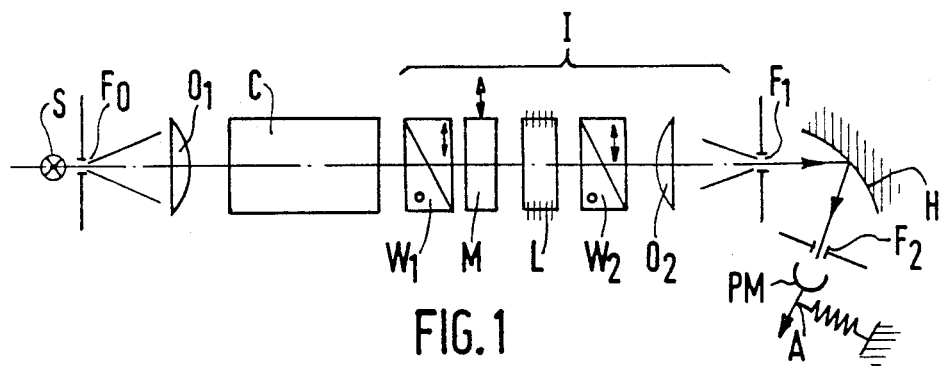
FIG. 1 is an embodiment of a device for the interferometric analysis of gas according to the invention.

In an embodiment selected and represented by the diagram of FIG. 1, the interferometric device according to the invention comprises a light source S, (for example, an iode quartz lamp for wave lengths greater than 280 nm or a deuterium lamp for wave lengths smaller than 280 nm), a source slot $F_0$; of two objectives $O_1$ and $O_2$ (each with a focal distance of 100 mm, for example), the optical axes of which coincide with and are aligned with the slot $F_1$, and, between these objectives, starting from $O_1$ successively, a gas cell C and an interferometric assembly or unit I, which will be described in further detail hereinbelow and, at its output, a slot $F_1$ upon which is formed the image of the slot $F_0$ through the objective $O_1$, the cell C, the interferometry unit I and the objective $O_2$). This slot $F_1$ constitutes the input slot of a holographic concave grating having a small radius of curvature, and is associated with an output slot $F_2$ disposed in front of the sensitive element of a detector PM which delivers a signal s once it is illuminated.

The interferometry unit I comprises two polarizing prisms $W_1$ and $W_2$, having a double image and of the same type and, between them, a birefringent plate L and a photoelastic modulator M. The two prisms $W_1$ and $W_2$ are two double image polarizing prisms of the same type, for example two Wollaston prisms or two Rochon prisms or analog. They can, for example, be made of magnesium fluorine their elements being adherent (and not stuck). $W_1$ and $W_2$ are Wollaston prisms as represented in FIG. 1.

The birefringent plate L is temperature-controlled for adjusting the path difference that it introduces.

The photoelectric modulator M is a silica or fluorine plate excited by a piezoelectric ceramic, thereby giving this plate a birefringency which is variable by compression. The optical axis of the modulator M is parallel to that of the plate L.

Figure 2:
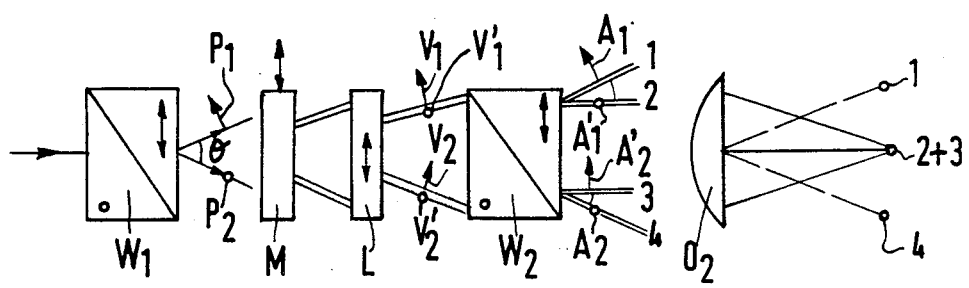
FIG. 2 is a detailed diagram of the device represented in FIG. 1.

FIG. 2 illustrates the working of the interferometry unit I, in which $W_1$ and $W_2$ are Wollaston prisms.

The prism $W_1$ delivers from a plane natural light wave two incoherent waves polarized perpendicularly along $P_1$ and $P_2$. The photoelastic modulator M and the birefringent plate L have the axes parallel and at 45° from $P_1$ and $P_2$ supplying two pairs of parallel polarization waves ($V_1$, $V'_1$) and ($V_2$, $V'_2$). The waves of each pair are coherent, dephased by $\phi$ and perpendicularly polarized (at 45° from $P_1$ or from $P_2$). The prism $W_2$ gives from each preceding pair two new pairs of two parallel waves that are parallely polarized.

At the output, therefore, pairs 1, 2, 3 and 4 are obtained. The two waves 1 interfere and are focalized by the objective $O_2$ at point 1, with an intensity proportional to $1+\cos\phi$ wherein $\phi$ is the phase angle difference between the waves. The two waves 4, in the same way, are focalized upon the point 4 with an intensity $1+\cos\phi$. Pairs 2 and 3 are parallel, focalized at the focal length of $O_2$ and have an intensity of $2(1-\cos\phi)$.

For exploitation of the present invention, it is necessary to isolate one of the three focalization points, preferably the focus of the objective $O_2$ is selected, since its image has an intensity which is double that of the other images. This double intensity is obtained through the appropriate placing of the slot $F_1$ (FIG. 1).

As will be seen hereinbelow, the device described immediately above can be applied to the simultaneous processing of several gases.

It will be noted that it is however necessary that the different gases sought present an absorption band in the same spectral zone, for example, the ultraviolet/visible range, 180 nm–1,000 nm, in order to be able to utilize a single source, a single detector and a single holographic grating.

Theoretically, to each fine gas structure corresponds an optimal thickness for the birefringent plate, but the tolerance on this thickness is not very restrictive. In fact, the regrowth of the fringes corresponding to a fine period $\delta\sigma$ structure ($\sigma$ being the number of waves equal to $1/\lambda$) occurs at a path difference of $$\Delta = 1/\delta\sigma$$

but several tens of fringes reappear with a clear contrast.

In the case of the $SO_2$ gas, $\Delta = e\Delta n = 100\lambda \pm 10\lambda$; e being the thickness and $\Delta n$ the birefringency.

There is a tolerance on e equal to $\Delta e = 10\lambda/\Delta n$; for $\Delta n = 10^{-2}$, $\lambda = 300$ nm (ultraviolet) or at $\Delta e = 0.3$ nm, thus the thickness e can be comprised between 2.7 and 3.3 mm.

The tolerance is that much greater as the spectrum is less periodic. Experiments have shown that with the same plate, it was possible to process simultaneously $SO_2$, $NO_2$, $NO$ and $O_3$, thereby presenting considerable interest for measurements in environment and for measurements upon emission.

If the same plate is not appropriate for the simultaneous processing of several gases, it is possible to juxtapose several plates of suitably selected thicknesses.

Figure 3:
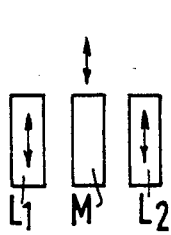
FIG. 3 is a schematic diagram of a detail of an embodiment of the device comprising two birefringent plates for the simultaneous processing of several gases.

For example, it is possible to place two plates as indicated in FIG. 3. The two birefringent plates $L_1$ (thickness $e_1$ and $L_2$ (thickness $e_2$) have their axes parallel and at 45° from those of the photoelastic modulator M.

This unit allows to dispose simultaneously of thicknesses $e_1+e_2$ and $e_1-e_2$.

Figure 4:
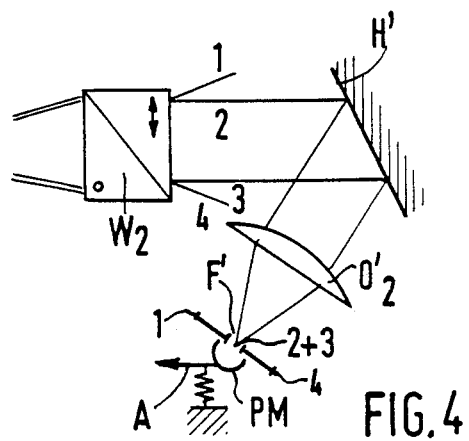
FIG. 4 is a schematic diagram, seen from below, of the output of a variant of the interferometric device according to the invention, utilizing a plane grating.

FIG. 4 illustrates a further embodiment of the interferometric device according to the invention, in which the concave holographic grating H is replaced by a plane grating H', engraved or holographic, placed directly behind the second Wollaston prism $W_2$, in such a way that the lines of this grating H' are horizontal, i.e. parallel to the plane of FIG. 4 (view from above of the device). The focalization objective $O_2$ of FIGS. 1 and 2, which is placed between the prism $W_2$ and a slot $F_1$, is replaced in the present example by an objective $O'_2$ following the grating H', which forms an image F' of the source slot $F_0$ on the sensitive element of the detector PM, this latter delivering a signal $\Delta$.

As explained hereinabove, a central image is obtained having the double intensity of those of the two lateral images and, preferably, this central image is utilized.

It will be well understood that the present invention is in no way limited to the embodiments described and represented hereinabove; it is adaptable to numerous variants available to the man skilled in the art without departing from the spirit and scope of said invention.

We claim:

1. Interferometric device for the detection and/or analysis of gas, of the type comprising an optical assembly forming the image of a luminous source (S) on the sensitive element of the detector, this image being formed through a cell (C) containing the gaseous mixture to be analyzed which is followed by an interferometry assembly (I) comprising a birefringent plate (L) and a modulating means located between an analyser and a polarizer followed by an interferential filter wherein, the analyser and the polarizer consist of two polarizing prisms ($W_1$ and $W_2$) the optical axes of which are perpendicular to that of the device and each give two photometrically identical images which are rectilinearly and perpendicularly polarized and the modulating means consist of a photoelastic modulator (M) comprising a silica or fluorine plate excited by a piezoelectric ceramic caused to vibrate in order to give said plate a birefringency variable through compression, having an axis parallel to that of the birefringent plate (L), the interferential filter being constituted by a grating multiplexer device (H, H').

2. The device according to claim 1, wherein the interferential filter is formed by a concave holographic grating having a small radius of curvature with an input slot which is the image of a source slot illuminated by the luminous source and an output slot conjugated of the input slot and placed opposite to the detector.

3. The device according to claim 2, wherein the input and the output slots are fixed, the grating rotates as a function of the spectral range selected.

4. The device according to claim 2, wherein one input slot corresponds to several output slot selected as a function of the desired spectral ranges, said output slots being capable of being shut as required.

5. The device according to claim 1, wherein the interferential filter is formed by a plane grating, engraved or holographic, disposed directly behind the second prism and followed by a focalization objective of a source slot illuminated by the luminous source, on an output source placed opposite the detector.

6. The device according to claim 1, wherein said bifringent plate comprises at least two bifringent plates.

* * * * *